US007022980B2

(12) United States Patent
Zavitsanos et al.

(10) Patent No.: US 7,022,980 B2
(45) Date of Patent: Apr. 4, 2006

(54) SPECTRAL AXIS TRANSFORM

(75) Inventors: A. Paul Zavitsanos, Westchester, PA (US); Philip Leigh Wylie, Kennett Square, PA (US); Chin-Kai Meng, Hockessin, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 127 days.

(21) Appl. No.: 10/768,044

(22) Filed: Feb. 2, 2004

(65) Prior Publication Data

US 2005/0167582 A1 Aug. 4, 2005

(51) Int. Cl.
*B01D 59/44* (2006.01)
*G01N 3/00* (2006.01)
*G06F 19/00* (2006.01)

(52) U.S. Cl. .................... 250/281; 250/282; 702/23; 702/27; 435/DIG. 9; 435/DIG. 1

(58) Field of Classification Search ............... 250/281, 250/282, 283, 288; 702/23, 27, 31; 210/198.2, 210/656
See application file for complete search history.

(56) References Cited

U.S. PATENT DOCUMENTS

| | | | | |
|---|---|---|---|---|
| 4,433,241 A | * | 2/1984 | Boesl et al. ............... 250/282 |
| 5,680,130 A | * | 10/1997 | Tsutsui et al. ............... 341/87 |
| 5,710,713 A | * | 1/1998 | Wright et al. ............... 702/23 |
| 6,147,344 A | * | 11/2000 | Annis et al. ............... 250/281 |
| 6,329,652 B1 | * | 12/2001 | Windig et al. ............... 250/282 |
| 6,581,013 B1 | * | 6/2003 | Annis et al. ............... 702/27 |
| 6,717,130 B1 | * | 4/2004 | Bateman et al. ............ 250/282 |
| 6,743,364 B1 | * | 6/2004 | van der Greef ............ 250/282 |
| 6,745,133 B1 | * | 6/2004 | Axelsson ..................... 702/27 |
| 2004/0096982 A1 | * | 5/2004 | Barnea et al. ............... 436/173 |
| 2004/0159783 A1 | * | 8/2004 | Gavin et al. ............... 250/282 |

* cited by examiner

*Primary Examiner*—Nikita Wells
*Assistant Examiner*—Johnnie L. Smith, II

(57) ABSTRACT

The invention relates to reference libraries of composite spectra that consolidate, into a single searchable data set, multiple independent spectra taken of a chemical compound under multiple conditions, generally on a single instrument. The reference libraries may be used, for example, to increase the analytical power of mass spectrometers such as API-CID mass spectrometers. The multiple independent spectra are converted into a composite spectrum by performing a number of steps. First, units on the x-axis of at least one, and generally all but one, of the independent spectra are renumbered so that the numerical range of the x-axes of the spectra do not perfectly overlap. Second, the x-axes of the independent spectra are aligned on a composite x-axis. Methods and programs for making and using the reference libraries and devices containing the reference libraries are also disclosed.

32 Claims, 5 Drawing Sheets

SPECTRAL AXIS TRANSFORM

BACKGROUND

1. Field of the Invention

The present invention relates to reference libraries of composite spectra that consolidate, into a single searchable data set, information from multiple independent spectra of a chemical compound taken under multiple conditions. The reference libraries may be used, for example, to increase the analytical power of mass spectrometers such as API-CID mass spectrometers.

2. Description of Related Art

A mass spectrometer (MS) is one of the most powerful tools available for quantitative and qualitative analysis of an unknown or suspect compound. One type of mass spectrometer, available since the 1950's, employs electron impact (EI) ionization and fragmentation—whereby vaporized molecules are simultaneously ionized and fragmented with high energy under high vacuum to produce a broad spectrum of ions. EI-MS is typically coupled to a gas chromatograph (GC) to insure adequate molecule separation prior to analysis. Spectra obtained by this technique provide unique spectral "fingerprints" of molecules that are reproducible under set conditions, e.g., 70 eV electron energy and approximately unit resolution.

With the increasing power and availability of computers, large collections, or libraries, of EI-MS spectra have been developed along with associated searching software. Such databases, which may contain hundreds of thousands of molecular fingerprints, are often purchased with the instrument. A typical library search compares the spectrum of an unknown compound with the spectra of known compounds in the library and retrieves "hits" of compounds that have similar spectra.

Unfortunately, GC separation, which is the separation technique usually employed with EI-MS, is not possible with a significant percentage of molecules. GC separation requires that molecules be injected as a vapor. Thus, large, thermally labile molecules are not always suitable for GC analysis. In addition, GC analysis, as often as not, requires extensive and time consuming sample preparation and derivatization. This is especially true in the case of compounds with high polarity and low volatility.

In contrast, liquid chromatography (LC) is a more versatile separation technique. For LC separation, the molecules are injected in solution. Most molecules of interest are more easily solubilized than vaporized. However, LC is not compatible with EI, where the molecule must be introduced into high vacuum as a vapor. Therefore, LC is coupled to mass spectrometers that utilize different mechanisms for ionization, e.g., atmospheric pressure ionization (API).

LC-API-MS is well suited to the investigation of semi-volatile, thermo-labile and polar substances, like pesticides, explosives and forensically relevant substances. Unfortunately, existing EI-MS libraries are not suitable for identifying API-MS spectra. New API-MS libraries must be constructed.

One difficulty in constructing libraries for API-MS is the fact that API, unlike EI, generates little or no fragmentation. It is not uncommon to see only the pseudo molecular ion in the mass spectra. This means that API-MS is an excellent means for identifying the molecular weight of an unknown compound, but it cannot distinguish between the thousands of molecules that have any given molecular weight.

To increase ion fragmentation, collision induced dissociation (CID) is typically used in combination with API-MS. However, CID is highly variable. The ions generated by CID, as well as the ion ratios, can vary between different mass spectrometer models, between instruments of the same model, and between day to day operations on the same instrument These variations occur, among other things, as a function of the ion source and the highly sensitive nature of the CID region.

One means for addressing the variable nature of API-CID-MS spectra is the use of performance based tuning. However, even when API-CIDMS is used in conjunction with performance based tuning, the vast array of molecules still vary considerably in their ability to fragment under any given conditions. Therefore, no single set of conditions permits the generation of adequate API-CID-MS spectra for every molecule.

To date, there have been two approaches toward generating reproducible API-CID-MS libraries with sufficiently wide applicability. A first approach generates a composite mass spectrum for a molecule that represents either the sum or the average of multiple spectra taken of the molecule at different CID voltages. However, this technique destroys an important piece of information for identifying the molecule, namely, the way its fragmentation changes relative to changing conditions. A second approach obtains three separate mass spectra of a molecule, each obtained at different CID voltages, and compares each spectrum to a separate library. However, this technique requires the user to sort through three, often contradictory, comparison results using relatively unreliable probability indices due to the few data points in each spectrum.

BRIEF SUMMARY OF THE INVENTION

The present invention relates to more informative and effective reference libraries of composite spectra, and methods for generating the same. Each composite spectrum in the reference library consolidates, into a single searchable data set, information from multiple spectra of a chemical compound taken under multiple conditions. The reference libraries may be used, for example, to enhance the analytical power of mass spectrometers such as API-CID mass spectrometers. Methods and programs for using the reference libraries, as well as devices containing said libraries, are also disclosed.

BRIEF DESCRIPTION OF THE DRAWINGS

To further illustrate the invention, reference is made to the following drawings.

The aforementioned drawings are not drawn to scale and common letters or numerals in the drawings designate identical subject matter from various vantage points.

DETAILED DESCRIPTION OF THE INVENTION

The present invention relates to reference libraries of composite spectra that consolidate, into a single searchable data set, information from multiple independent spectra of a chemical compound taken under multiple conditions using a single analytical technique, e.g., LC-API-CID-MS. The reference libraries are particularly useful as a means of increasing the analytical power of API-CID mass spectrometers, and especially LC-API-CID-MS, since each spectrum changes as a function of increasing collision energy in a manner that is characteristic of the molecule. However, the reference libraries can be utilized to consolidate, into a single searchable data set, information derived under multiple conditions using another analytical technique, including, but not limited to, any one of the following analytical techniques: ultraviolet spectrometry; nuclear magnetic resonance spectrometry; infrared spectrometry; and, more particularly, other types of mass spectrometry, including EI-MS In a first embodiment, there is a method for generating a reference library of composite spectra. The method includes a number of steps.

A recommended preliminary step is performance based tuning. API-CID-MS spectra are often inconsistent between instruments of different suppliers and even between different units of the same model due to variabilities within the CID region of the machine. For example, if the length of the CID region varies by as little as 100 microns between two instruments, the spectra will vary. Similarly, if the vacuum pump gets dirty, the pressure of neutral gas within the CID region may rise, causing the spectra to vary. Also, if the electrostatic lens gets dirty, the spectra will vary. Thus, a given voltage setting does not necessarily correspond to a given ion energy level within the instrument. Performance (fragmentation) based tuning does not rely on a voltage value to set the ion energy. Instead, performance based tuning relies on tuning the instrument to a fixed performance variable, in this case a specified fragmentation, using predefined chemical compounds.

Performance based tuning is not always necessary. For example, in the. case of API-CID-MS, when generating small libraries of composite spectra for use in verifying the identity. of a compound whose spectra will be run shortly thereafter on the same machine, performance based tuning is not required. In addition, performance based tuning may not be required when the creating libraries for use with other spectrometer devices that are less variable. However, performance based tuning is recommended in most API-CID-MS applications given the sensitivity of the CID region and its impact on the resultant spectra.

Performance based tuning for API-CID-MS has been described in the prior art. The tuning compounds selected should give an informative spectrum with reproducible parent/product ion ratios at the specified condition, e.g., fragmentation voltage. In the case of variable voltage, at least one tuning compound should be used at each voltage to insure adequate tuning across the entirety of voltages employed. To determine adequate tuning, a control chart for the ion ratios is maintained which identifies the degree of acceptable variation. As long as the ion ratios for each of the performance based tuning compounds are within the specified limits, spectra for new library entries can be created.

The tuning compound utilized may be a compound selected from the class of compounds already characterized in the reference library or it may be something completely removed from the compound classes in the library. However, the spectrum of the tuning compound must display the parent ion and at least one product ion. In addition, a change in the fragmentation voltage should produce a significant change in the spectrum. A number of suitable compounds for this purpose are known. For example, for the generation of pesticide libraries on APICID-MS using voltages of 60, 120, 180 and 240, azinphos-methyl can be employed as a tuning molecule at 60V, benomyl can be employed as a tuning molecule at 120 V, flumetsulam can be employed as a tuning molecule at 180 V, and siduron can be employed as a tuning molecule at 240 V. The voltages are then modified to produce the closest match to the ion ratios specified for each fragmentation standard and these measured voltages are the voltages utilized to create library entries.

A first step in formulating the reference library is acquiring multiple independent spectra for a known chemical compound under multiple predefined instrument conditions. Preferably, all of the spectra for the known chemical compound are obtained on a single instrument using a single sample injection. However, it is also possible, though less preferable, to use multiple sample injections and, even less preferably, multiple sample injections into multiple instruments appropriately tuned. Each spectrum includes an x and a y axis which, in the case of mass spectrometry, represents the m/z ratio and abundance (or normalized relative abundance), respectively, of detected ions.

Any number of multiple independent spectra can be acquired. Preferably, at least three spectra, and more preferably at least four spectra, are obtained. There is no upper limit on the number of spectra that can be utilized in this method although there may be a point of diminishing returns.

In the case of API-MS-CID, the preferred variable instrument condition is CID voltage. One or more other conditions, however, such as target gas pressure, can also be selected for variation. Ideally, four spectra at four CID voltages are acquired in a single run since this is within the capability of many commercially available mass spectrometers, such as the Agilent 1100 LC/MSD SL. Alternatively, multiple runs can be employed at different CID voltages involving multiple sample injections.

Preferably, the CID voltages selected run from low to medium to high voltage in order to cover a wide range of collision energies. At low energy, the protonated molecular ion and other adduct ions (first order ions) are typically the dominant ions in the spectrum obtained. At higher energies, fragmentation of the protonated molecular ion and other adducts occurs, adding product ions (second order ions) to the spectrum. Eventually, at sufficiently high voltage, the spectrum is populated by simple ions. The group of spectra taken at different energies, together, define a spectral progression from low to high energy that is highly characteristic of the molecule. Some molecules exhibit a gradual change in their spectra with rising collision energy. Other molecules exhibit a water fall effect, where there is a rapid progression from little information to a wealth of information over a narrow change in collision energy.

In general, the minimum fragmentation voltage required is that which will give a protonated molecular ion with little fragmentation for the most fragile of the expected compounds. Similarly, the maximum fragmentation voltage is generally that which will give an informative spectrum with a significant amount of fragmentation for the most difficult to fragment compound expected, but which still allows the molecular ion to be measured. Obviously, these parameters can vary greatly depending on the diversity of the library. The more diverse the library, the wider the voltage range that needs to be employed.

For example, a range of voltages generally suitable for generating pesticide libraries is 60V (Low 1), 120V (Low 2), 180 V (Medium) and 240 V (High). In addition, a range of voltages generally suitable for generating drug libraries is 75 V (Low 1), 150 V (Low 2), 225 V (Medium) and 300 V (High).

Preferably, only one instrument condition is varied. Thus, for example, if the voltage is varied in an APICID-MS, the mobile phase composition should remain the same. This is, in part, because the interpretation of spectra obtained by API-CID-MS can be complicated by the formation of adducts and the mobile phase composition may affect the types of adducts formed and the extent of their formation. There are ways known in the art to deal with adduct formation. Nonetheless, it remains preferable to minimize spectral variation by creating libraries specific to a given mobile phase chemistry for best-match performance. Other instrument conditions that generally remain the same in this embodiment include target gas pressure.

A second step for formulating the reference library renumbers the units on the x-axis of at least one of the independent spectra so that the numerical range of the x-axis of the independent spectra do not perfectly overlap. More preferably, there is no overlap whatsoever. In fact, it is often desirable to renumber the x-axes of the individual spectra so that there is actually a predefined separation between the x-axis of each spectrum. Generally, the units on the x-axes of all but one of the independent spectra are renumbered in this manner. This step is referred to as "axis shifting." The exact amount of axis shifting is not important as long as it is consistent throughout the library and sufficient to prevent perfect spectral overlap.

For example, if four spectra at four different voltages are scanned from a mass to charge ratio (m/z) of 1 to 1000, three of those spectra might be renumbered 1001 to 2000, 2001 to 3000 and 3001 to 4000, respectively. Alternatively, three of the spectra might be renumbered 2001 to 3000, 4001 to 5000 and 6001 to 7000 to create a defined separation between the x-axes. The renumbering and spacing does not matter as long as it is consistent throughout the library.

A third step for formulating the reference library generates a composite spectrum for the known chemical compound from the axis shifted independent spectra by aligning the x-axes of the axis shifted independent spectra on a composite x-axis. This step can be performed concurrently with, or subsequent to, axis shifting. The y-axis of the composite spectrum, which is generally identical to the y-axis for the individual spectra, does not require axis shifting. Thus, if the y-axis represents the abundance or normalized abundance of ions in the individual spectra, as is the case in mass spectrometry, the y-axis continues to represent the abundance of ions or normalized abundance on the composite spectrum. The y-axis data from the individual spectra can be recorded on the composite spectrum without manipulation.

The entire process is called "spectral axis transform." Spectral axis transform can be done in a number of ways. For example, spectral axis transform can involve 1) aligning multiple spectra end-to-end on a single axis, 2) aligning the spectra on a transformed axis with defined spaces between the spectra (e.g., four spectra obtained over a 1 to 1000 u mass range could be placed on a new axis in the following m/z ranges: 1 to 1000, 2001 to 3000, 4001 to 5000, and 6001 to 7000), or 3) aligning the spectra so that they overlap but are offset so that the overlap is not perfect. The amount of offset could be as little as one mass unit or as much as 999 mass units for a spectrum collected over a 1 to 1000 mass range. For example the transformed axis could plot four spectra (collected over a range of 1 to 1000 u) as follows: 1 to 1000, 2 to 1001, 3 to 1002, and 4 to 1003. Alternatively, they could be plotted in this way: 1 to 1000, 701 to 1700, 1401 to 2400, and 2101 to 3100. In the first example, the spectra are overlaid, but each is offset by 1 u from the previous one. In the second example, the spectra are overlapped and each is offset by 700 u from the previous one. Some mass spectrometers (such as Agilent's Time of Flight MSD) measure masses with high resolution. In this case, the offset could be less than one mass unit. In fact, the offset could be as small as $\Delta m$ where $\Delta m$ is the mass spectral peak width at half height. For example, using a high-resolution mass spectrometer, four spectra (collected from 1 to 1000 u) could be overlapped on a transformed axis as follows: 1.0000 to 1000.0000, 1.0001 to 1000.0001, 1.0002 to 1000.0002, and 1.0003 to 1000.0003. In this case, the spectra are each offset by 0.0001 mass unit. This works because the high-resolution mass spectrometer can resolve such small differences in mass between two different ions. In all cases when spectra are overlapped, they must be offset by at least the mass spectral peak width or they will be superimposed and information will be lost. Conversely, by offsetting spectra, the possibility of peak overlap is reduced and most (or all) of the information is retained. Of course, the best way to eliminate any overlap in mass spectral peaks and, therefore, to retain all of the spectral information, is to transform the x-axis so that there is no overlap at all.

Preferably, the composite spectrum is then stored in a computer readable medium. For this purpose, any computer readable medium known in the art is sufficient.

The process can be repeated an infinite number of times for an infinite number of known chemical compounds to generate libraries of infinite size. In one embodiment, the library is focused on a specific field of compounds, e.g., pesticides. However, much broader libraries are also embraced.

Not all of the aforementioned steps need to be performed in the same contemporaneous operation. For instance, in one embodiment, multiple independent spectra for a known chemical compounds are taken under multiple predefined instrument conditions and stored as an intermediate database and this process can be repeated for a number of compounds. Next, a purchaser of the database, when using the database, inputs the spectral conditions that he wishes to compare as well as the parameters for running the comparison, e.g., the parameters for axis shifting and/or parameters for spacing the spectra on the x-axis of the composite spectrum. Composite spectra for the known compounds in the library are then generated, on demand, in accordance with the input spectral conditions and comparison parameters. Alternatively, all of the steps for generating the reference library can be performed in the same operation. The library can then be provided to a user as a collection of pre-formed composite spectra that cannot be manipulated, or at least, cannot be manipulated as easily as the library formed on demand.

In a second embodiment, there is a reference library of composite spectra, preferably stored on a computer readable medium, generated in the manner described above. The reference library may be sold as a stand alone item. The reference library may also be sold in combination with software for searching, supplementing and/or manipulating data therein and/or in combination with an instrument, such as a API-CID mass spectrometer.

In a third embodiment, there is provided a method of identifying an unknown chemical. The method includes a number of steps.

A recommended, but not required, preliminary step is performance based tuning. This is especially true when API-CID-MS is used to identify the unknown compound. The performance based tuning is done in the same manner previously described. The identities of the tuning molecules employed are not particularly important as long as they can be used to match spectra generated on the instrument to library spectra. Preferably, the tuning molecules employed are those utilized in the generation of spectra in a reference library, such as that described above.

In a first step, multiple independent spectra are acquired for the unknown chemical compound, under multiple predefined instrument conditions. Preferably, all spectra for the unknown compound are obtained on a single instrument with a single injection. However, it is also possible, though less preferable, to use multiple sample injections and, even less preferably, multiple sample injections into multiple instruments appropriately tuned. Each spectrum includes an x and a y axis which, in the case of mass spectrometry, represents the mass to charge ratio and abundance, respectively, of detected ions.

In a second step, the units on the x-axis of at least one of the independent spectra are renumbered, or axis shifted, so that the numerical range of the x-axis of the independent spectra do not perfectly overlap. Generally, the units on the x-axes of all but one of the independent spectra are renumbered in this manner.

In a third step, a composite spectrum for the unknown chemical compound is generated from the independent spectra by aligning the x-axes of the independent spectra on a composite x-axis. This can be done concurrently with, or subsequent to, the axis shifting step.

Fourth and finally, the composite spectrum of the unknown chemical compound is compared to the composite spectra of known chemical compounds, preferably stored in, or generated from, a reference library. In one embodiment, the reference library of composite spectra is compiled at the time of the comparison. For instance, in one embodiment, multiple independent spectra for a known chemical compound are taken, generally on a single instrument, under multiple predefined instrument conditions and stored as an intermediate database. Next, a purchaser, when using the database to identify an unknown compound, inputs the spectral conditions that he wishes to compare as well as the parameters for the comparison, e.g., parameters for axis shifting data and/or parameters for spacing the spectra on the composite x-axis. The composite spectra in the library are then generated, on demand, in accordance with the input spectral conditions and comparison parameters. Alternatively, all of the steps for generating the reference library can be performed in the same operation and the library provided to a user as a collection of pre-formed composite spectra that cannot be manipulated, or at least, cannot be manipulated as easily as the library formed on demand.

In either case, the parameters used to form the composite spectrum for the unknown chemical compound should be the same as the parameters used to form the composite spectra for known chemical compounds in the reference library, including the parameters for axis shifting the data and, optionally, spacing the data on the composite spectra.

The comparison may be performed using any pattern matching algorithm, such as a linear regression algorithm. Preferably, the algorithm generates a probability index that assesses the quality of each hit. Due to the increased number of data points in the composite spectra, the reliability of the probability indices generated is significantly improved.

In this method, the number of spectra, and the conditions in which the various spectra are obtained, are only limited by the library utilized. However, there needs to be a correspondence between the conditions under which the library entries are generated and the conditions under which the spectra for the unknown compound is generated. For example, if four CID voltages (as modified by performance based tuning) are used to make the independent spectra used to generate the composite spectra for all the known chemical compounds in the reference library, then those are the CID voltages (as modified by performance based tuning) that should be employed to make the independent spectra used to generate the composite spectra for the unknown chemical compound.

The allowances for variations due to performance based tuning compensates for differences between the settings and actual conditions within the instrument. For example, if it is determined that CID voltages of 63 V, 85 V, 122 V and 179 V are required on the instrument to match spectra for tuning molecules recorded at 60 V, 80 V, 120 V and 180 V, respectively, then 63 V, 85 V, 122 V and 179 V are the voltages that should be employed to make the individual spectra for the unknown compound. The key is to make the internal conditions with the instrument correspond to the internal conditions used to make each entry in the library.

Preferably, the only instrument conditions that are varied to make the composite spectra of the unknown compound are those that were varied to make the composite spectra in the reference library. For example, if the voltage is varied in an API-CID-MS, the mobile phase composition and internal target gas pressure preferably remains the same.

In a fourth embodiment, there is a computer readable medium including instructions to cause a computer to perform a number of functions. First, the instructions on the computer readable medium cause the computer to receive multiple spectra for an unknown chemical compound, generally taken on a single instrument, under multiple predetermined conditions. Second, the instructions on the computer readable medium cause the computer to axis shift at least one, and generally all but one, of the multiple spectra. Third, the instructions on the computer readable medium causes the computer to generate a composite spectrum for the unknown chemical compound. This can be done concurrently with, or subsequent to, the axis shifting step. Due to the axis shifting step, there is not perfect overlap in the data of the independent spectra on the composite spectra. Fourth, the instructions on the computer readable medium cause the computer to compare the composite spectrum for the unknown chemical compound to one or more known chemical compounds stored in, or derived from, a reference library. In one embodiment, the computer readable medium additionally includes a reference library.

In a fifth embodiment, there is a device for identifying an unknown chemical compound. The device includes a reference library of composite spectra, generally stored on a first computer readable medium as described above. The device also includes a spectrometer and a computer. Finally, the device includes a second computer readable medium, which may be the same as the first computer readable medium, which causes the a computer to receive multiple spectra, axis shift the spectra, and generate a composite spectrum for an unknown chemical compound, as described above, and then compare the composite spectrum for the unknown chemical compound to composite spectra for known chemical compounds in the reference library.

ILLUSTRATIVE EXAMPLES

In a LC-API-MS, an unknown compound is received in liquid form by an LC coupled to a mass spectrometer and analyzed. The unknown compound is ionized using API. Usually, API returns a spectrum showing a single MS peak for the pseudo molecular ion. Accordingly, the degree of fragmentation is increased by CID, which fragments the single ion. CID usually produces three to four products, which may or may not include the parent molecular ion. Fragmentation occurs at different energies for different ions.

In order to produce spectra showing more than a single MS peak (excluding adducts), which represents the pseudo molecular ion, the unknown compound may be injected into the mass spectrometer, and scanned multiple times at different collision energies in a CID region, yielding multiple spectra representing the unknown compound. For example, four spectra can be obtained by scanning the compound four times at four energy levels.

Figure 1A:
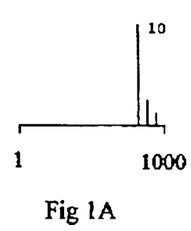
FIGS. 1A, 1B, 1C and 1D depict mass spectra for a chemical compound obtained under different conditions on the same instrument.
Figure 1B:
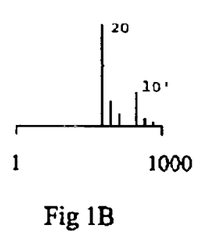
Figure 1C:
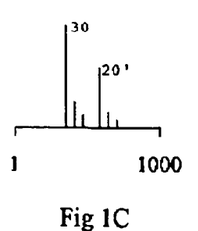
Figure 1D:
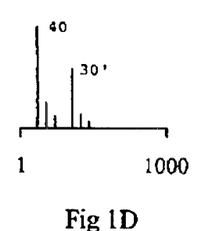

This concept is visually represented by the multiple independent mass spectra in FIGS. 1A–D. In each of FIGS. 1A–D, the x-axis is the mass to charge ratio (m/z) and the y-axis is the abundance or normalized relative abundance of detected ions, respectively. FIG. 1A is a first mass spectrum, obtained at a relatively low collision energy. FIG. 1A contains a series of MS peaks for the parent molecular ion (10). FIG. 1B is a second spectrum, obtained at a higher collision energy. FIG. 1B contains a diminished series of MS peaks for the parent molecular ion (10'), and a new series of MS peaks for a first order fragment ion of the parent molecular ion (20) which appear earlier on the m/z axis. FIG. 1C is a third spectrum taken at an even higher collision energy. FIG. 1C contains no MS peaks for the parent molecular ion. Instead, FIG. 1C contains a diminished series of MS peaks for the first order fragment ion (20') as well a new series of MS peaks for a second order fragment ion (30), which is basically a fragment of the fragment and appears at lower m/z on the m/z axis. FIG. 1D is a fourth spectrum taken at the highest collision energy. FIG. 1D contains a diminished series of MS peaks for the second order (30') fragment and a new series of MS peaks for a third order fragment ion (40), which appears even earlier on the m/z axis. It should be recognized that the spectra in FIGS. 1A–D are vastly simplified and do not fully show isotopes, adducts and other information that might otherwise appear.

As evident in FIGS. 1A–D, as more energy is applied by an increase in fragmentation voltage, the parent ion breaks down into product ions. These product ions are specific fragments of the parent ion. As even more energy is applied to the ions, some product ion species will themselves be fragmented. As a consequence, some product ions are apparent only over a narrow range of fragmentation voltages. At the highest voltages, the ions produced are typically simple, low m/z ions. How the ions fragment over the variable energy levels, is highly informative.

Each spectrum of FIGS. 1A–D has low information content and is likely to produce multiple hits in a library search. Furthermore, each distinct spectrum fails to show the progression, or chain, of fragmentation that is evident from viewing all of the spectra.

However, a composite spectrum formed from the four independent spectra of FIGS. 1A–D is much more informative. Furthermore, a composite spectrum of the four independent spectra documents the progression of fragmentation which is very characteristic of a molecule. It should be noted that the order of the spectra in the composite spectrum can be reversed or out of sequence as long as the same order is used for the comparison library generated for spectral matching.

Figure 2:
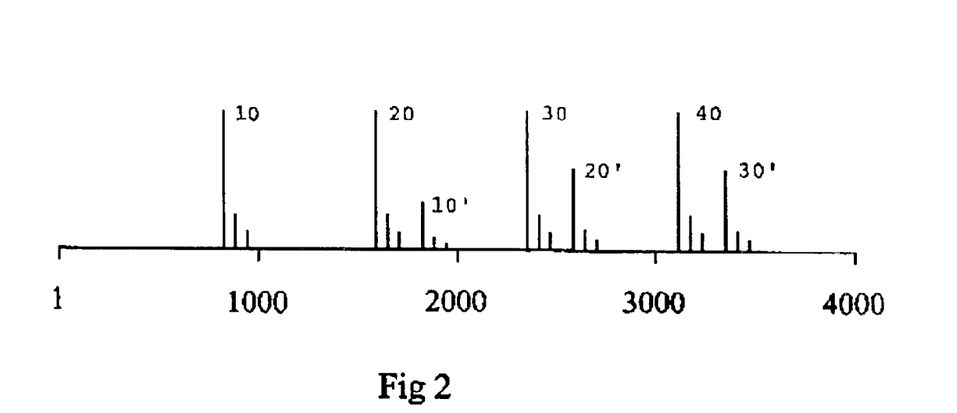
FIG. 2 illustrates a composite spectrum derived from the mass spectra in FIGS. 1A, 1B, 1C and 1D.

This concept is illustrated in FIG. 2 which shows a composite spectrum of the multiple individual spectra described in FIGS. 1A–D. As in FIGS. 1A–D, the x-axis is the m/z axis and the y-axis is the abundance axis. However, the x-axis of FIG. 2 is variable, and may be adjusted or defined by the user, or set to a default. In FIG. 2, the x-axis shows all four spectra from FIGS. 1A–D on a single m/z axis, the x-axis information on all but FIG. 1A having been axis shifted. The degree of the axis shift can be chosen based upon the size of the spectra or upon the range of the instrument and may be any value. The spectra after axis shifting can even overlap so long as they are not exactly superimposed, but this is less desirable. In this embodiment, the spectrum of FIG. 1A is separated from the spectrum of FIG. 1B by 1000, as is the spectrum of FIG. 1C from FIG. 1B and the spectrum of FIG. 1D from FIG. 1C. Thus, the composite axis in the spectrum of FIG. 2 runs from 1 to 4000 m/z where the x-axis in the spectra of each of FIGS. 1A–D runs from 1 to 1000 m/z.

The single composite spectrum of FIG. 2 has high information content and includes all the spectral information for a particular compound. Thus it permits much better discrimination when attempting to match an unknown to a library spectrum. In a searchable library, the spectrum of FIG. 2 should produce hit lists that have reliable probability indices. This is because a matching algorithm, e.g., a linear regression algorithm, using more points is typically more reliable than a matching algorithm using fewer points. Also, the composite spectrum shows the spectral change of the unknown compound during fragmentation at different collision energies which is highly characteristic of the compound and aids the researcher in deciding whether a given hit is, in fact, a match.

When searching a library containing composite spectra similar to the composite spectrum of FIG. 2, an independent search could first match the parent ion, and then subsequently search the subset of library entries identified for associated fragment ions in the composite spectra. Alternatively, each composite spectrum could be searched as a whole using any known pattern matching search technique.

Additionally, when searching a database containing composite spectra similar to the composite spectrum of FIG. 2, the search may measure, organize and report hits by a correlation of how many of the MS peaks stored in the library entries match the unknown composite spectrum in m/z value and relative abundance, e.g., four of four matches would have the highest correlation, three of four matches would have the next highest correlation, two of four matches would have a lower correlation, etc. This can be accomplished using an algorithm to match the composite spectrum to compounds in a library consisting of composite spectra. A perfect match has the same ions with the same relative ion abundances as the library spectrum.

In a library containing composite spectra, the spectra may be stored exactly as shown in FIG. 2, or may be stored so that the x-axis is variable and may be defined by the user or set to a default. Alternatively, the independent spectra used to form the composite may be stored separately and the composite spectra generated, on demand, in a manner defined by the user or set to a default.

Figure 3:
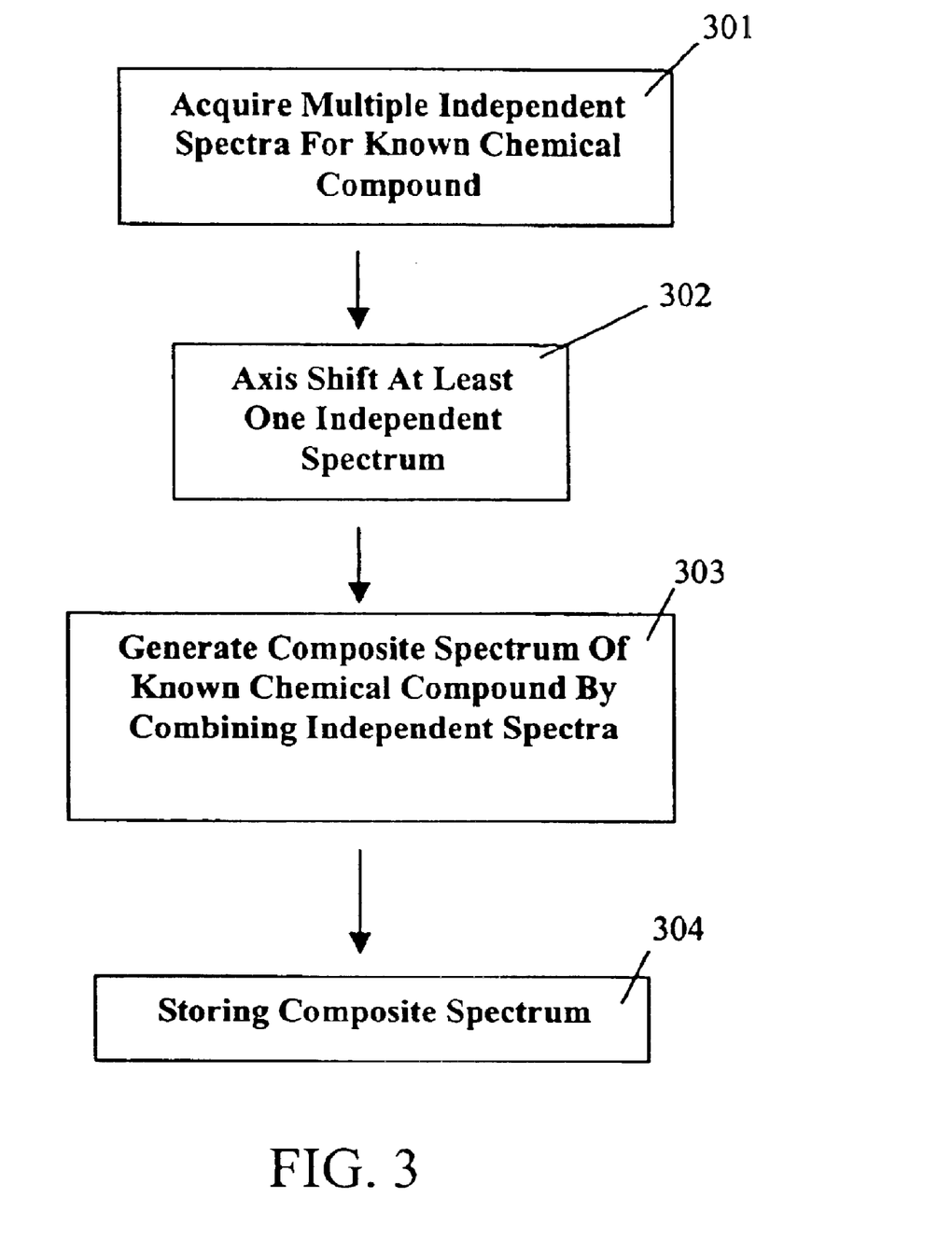
FIGS. 3, 4 and 5 are flow charts that show embodiments of the architecture, functionality, and operation of possible implementations of software that can be used to operate the systems and methods described herein.
Figure 4:
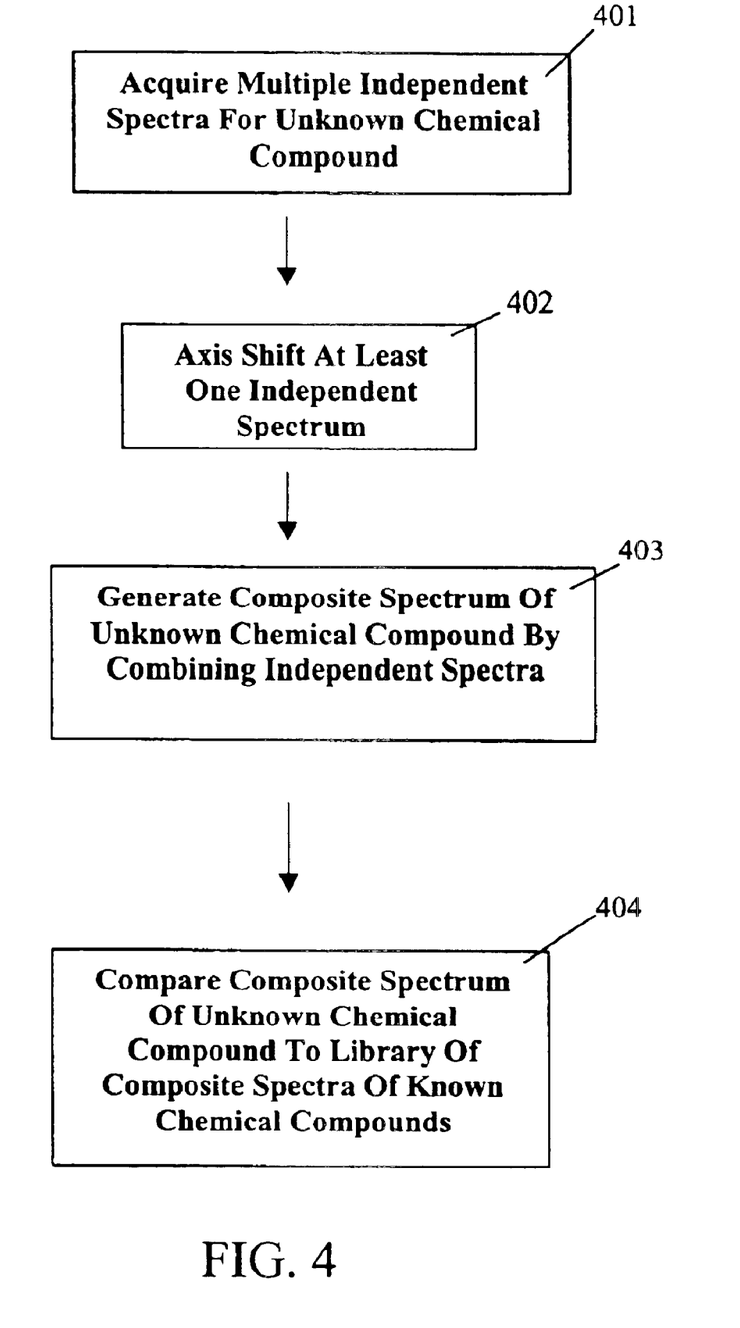
Figure 5:
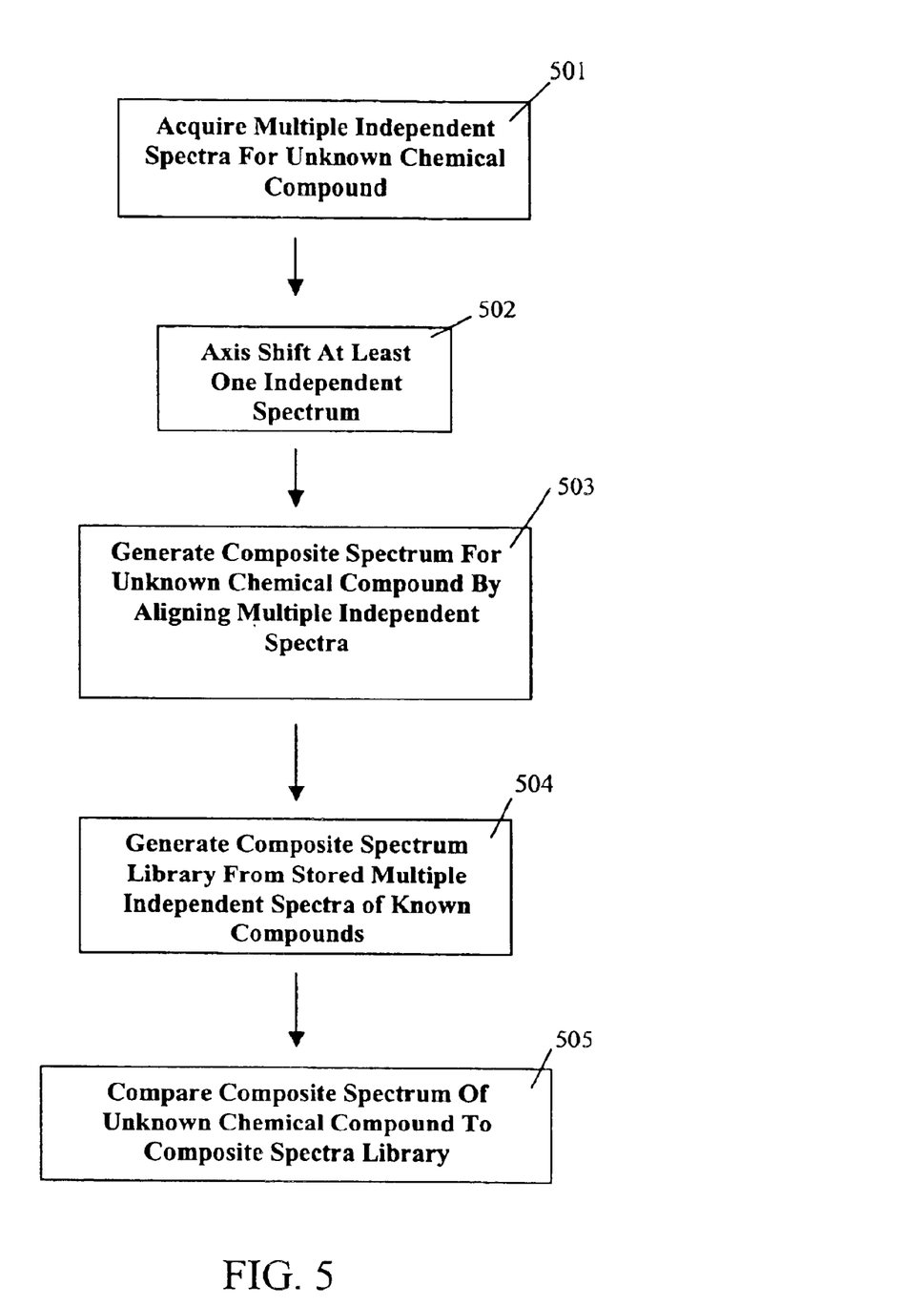

The flow charts of FIGS. 3, 4 and 5 show embodiments of the architecture, functionality, and operation of possible implementations of software that may be used to operate the systems and methods described herein. In this regard, each block may represent a module, segment or portion of code, which includes one or more executable instructions for implementing the specified logical functions. It should be noted that in some implementations, the functions noted in the blocks may occur out of the order indicated by the figures. For example, two blocks shown in succession may in fact be executed substantially concurrently or the blocks may sometimes by executed in reverse order, depending upon the functionality involved, as would be understood by those reasonably skilled in the art of the present invention.

Figure 6:
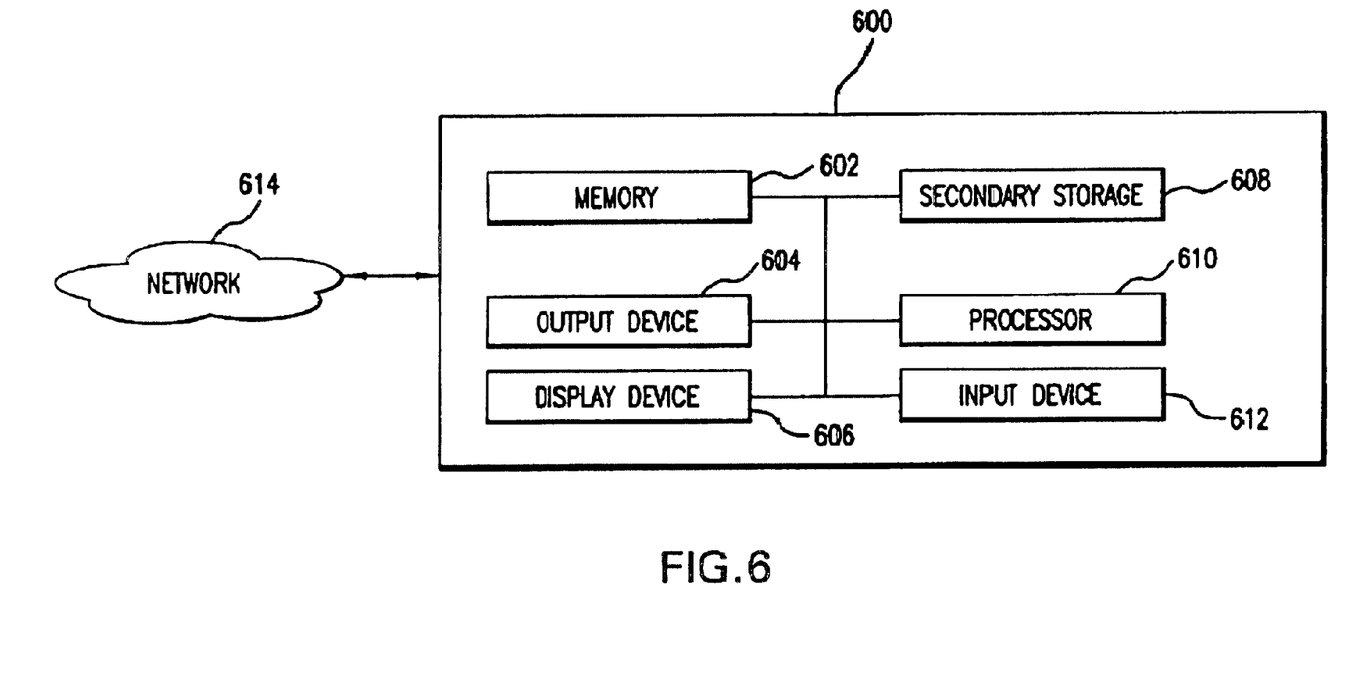
FIG. 6 illustrates exemplary hardware components of a computer that may be used to perform comparative library searching.

FIG. 6 illustrates exemplary hardware components of a computer 600 that may be used to perform the comparative library searching. The computer 600 includes a connection with a network 614 such as the Internet or other type of computer or telephone networks. The computer 600 typically includes a memory 602, a secondary storage device 608, a processor 610, an input device 612, a display device 606, and an output device 604.

The computer system 600 may be a general purpose computer system which is programmable using a high level computer programming language, such as "C," "C++" "Pascal," "Visual Basic" or other language. The computer system may also be specially programmed, special purpose hardware. In a general purpose computer system, the processor 610 is typically a commercially available processor, of which the series x86 processors, including a Pentium processor using MMX extensions available from Intel, and the 680X0 series microprocessors available from Motorola are examples. Many other processors are available. Such a microprocessor executes a program called an operating system, of which Windows95, WindowsNT, Windows 2000, Windows XP, UNIX, DOS and VMS are examples, which controls the execution of other computer programs and provides scheduling, debugging, input/output control, accounting, compilation, storage assignment in a file system containing named files of data, data management and memory management, communication control, protection and related services. The processor 602 and operating system define a computer platform for which application programs in high-level programming languages are written. It should be understood that other embodiments may employ other computer platforms, processors, or high-level programming languages. Additionally, the computer 600 may be a multiprocessor computer system or may include multiple computers connected over a computer network or incorporated into the MS system.

The memory 602 may include random access memory (RAM) or similar types of memory. The secondary storage device 608 may include a hard disk drive, floppy disk drive, CD-ROM drive, magnetic disk, flash memory, tape or other types of non-volatile data storage, and may correspond with various databases or other resources. The disk may be removable, known as a floppy disk, or permanent, known as a hard drive. A disk has a number of tracks in which signals are stored, typically in binary form, i.e., a form interpreted as a sequence of ones and zeros. Such signals may define, for example, an application program to be executed by the microprocessor, or information stored on the disk to be processed by the application program.

The processor 610 may execute information stored in the memory 602, the secondary storage 608, or received from the Internet or other network 614. Typically, in operation, the processor 610 causes data to be read into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and copies the data to and from the disk if the data are not being used. A variety of mechanisms are known for managing data movement between the disk and the integrated circuit memory element, and any such mechanisms may be employed. Similarly, any memory system may be employed.

The input device 612 may include any device for entering data into the computer 600, such as the mass spectrometer utilized by the Systems And Methods For Mass Spectrometry Dynamic Library Searching, a keyboard, keypad, cursor-control device, touch-screen (possibly with a stylus), or voice command device. The display device 606 may include any type of device for presenting visual image, such as, for example, a computer monitor, flat-screen display, or display panel. The output device 604 may include any type of device for presenting data in hard copy format, such as a printer, and other types of output devices including speakers or any device for providing data in audio form. The output device 604 could be a file read by the same or another computer. The computer 600 can possibly include multiple input devices, output devices, and display devices.

Although the computer 600 is depicted with various components, one skilled in the art will appreciate that the computer 600 can contain additional or different components. In addition, although aspects of an implementation consistent with the present disclosure are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; or other forms of RAM or ROM. The computer-readable media may include instructions for controlling the computer 600 to perform a particular method.

The foregoing description is provided to explain and illustrate the invention but is not intended to be exhaustive or to limit the invention to only those embodiments disclosed. For example, the invention has been described primarily in connection with LC-API-CID-MS. However, it should be understood that the invention is equally applicable to any type of analysis that produces different spectra for compounds under different conditions. Accordingly, many modifications and variations are possible consistent with the above teachings.

What is claimed is:

1. A method of generating a reference library of composite spectra including the following steps:
   (i) acquiring multiple independent spectra for a known chemical under multiple instrument conditions, each independent spectrum including an x and y axis;
   (ii) renumbering the units on the x-axis of at least one of the independent spectra so that the x-axes of the independent spectra do not perfectly overlap; and
   (iii) generating a composite spectrum for the known chemical by aligning the x-axes of the independent spectra on a composite x-axis.

2. The method of claim 1, additionally including the step of storing the composite spectrum on a computer readable medium.

3. The method of claim 1, where the independent spectra are stored in an intermediate reference library and the remaining steps for creating the composite spectrum are performed, on demand, in response to inputs by a user regarding desired spectral conditions, renumbering and/or intervening spacing units.

4. The method of claim 1, where the independent spectra are obtained on a mass spectrometer, where the x-axes for the independent spectra represent the mass to charge ratio (m/z) and where the y-axes for the independent spectra represent the abundance of detected ions or normalized relative abundance.

5. The method of claim 4, where said mass spectrometer utilizes atmospheric pressure ionization (API) and collision induced dissociation (CID) fragmentation.

6. The method of claim 5, where said mass spectrometer is coupled to a liquid chromatograph (LC).

7. The method of claim 5, where said multiple predefined instrument conditions are different CID voltages.

8. The method of claim 5, where the mass spectrometer is tuned with one or more tuning compounds prior to acquiring the independent spectra.

9. A reference library of composite spectra created in the following manner:
  (i) acquiring multiple independent spectra for a known chemical under multiple instrument conditions, each independent spectrum including an x and y axis;
  (ii) renumbering the units on the x-axis of at least one of the independent spectra so that the x-axes of the independent spectra do not perfectly overlap; and
  (iii) generating a composite spectrum for the known chemical from said independent spectra by aligning the x-axes of the independent spectra on a composite x-axis.

10. The reference library of claim 9, where said library is stored on a computer readable medium.

11. The reference library of claim 9, where the independent spectra are stored in a database and the remaining steps for forming the reference library of composite spectra occur, on demand, in response to inputs by a user regarding desired spectral conditions, renumbering and/or intervening spacing units.

12. The reference library of claim 9, where the independent spectra are obtained on a mass spectrometer, where the x-axes for the independent spectra represent the mass to charge ratio (m/z) and where the y-axes for the independent spectra represent the abundance of detected ions or normalized relative abundance.

13. The reference library of claim 12, where said mass spectrometer utilizes atmospheric pressure ionization (API) and collision induced dissociation (CID) fragmentation.

14. The reference library of claim 13, where said mass spectrometer is coupled to a liquid chromatograph (LC).

15. The reference library of claim 13, where said multiple predefined instrument conditions are different CID voltages.

16. The reference library of claim 13, where the mass spectrometer is tuned with one or more tuning compounds prior to acquiring the multiple independent spectra.

17. A method of identifying an unknown chemical including the following steps:
  (i) acquiring multiple independent spectra for an unknown chemical under multiple instrument conditions, each independent spectrum including an x and y axis;
  (ii) renumbering the units on the x-axis of at least one of the independent spectra so that the x-axes of the independent spectra do not perfectly overlap;
  (iii) generating a composite spectrum for the unknown chemical from said independent spectra by aligning the x-axes of the independent spectra on a composite x-axis; and
  (iv) comparing the composite spectrum of the unknown chemical to the composite spectra of one or more known chemicals.

18. The method of claim 17, where step (iv) compares the composite spectrum of the unknown chemical to the composite spectra of one or more known chemicals stored in a reference library.

19. The method of claim 17, where step (iv) compares the composite spectrum of the unknown chemical to the composite spectra of one or more known chemicals generated from a reference library that contains multiple independent spectra of known chemicals taken under multiple instrument conditions.

20. The method of claim 17, where the comparing step is performed by a pattern matching algorithm.

21. The method of claim 17, where the comparing step generates a probability factor quantifying the probability that the unknown chemical corresponds to a chemical represented by a composite spectrum in the reference library.

22. The method of claim 17, where said independent spectra are obtained on a mass spectrometer, where the x-axes for the independent spectra represent the mass to charge ratio (m/z) and where the y-axes for the independent spectra represent the abundance of detected ions or normalized relative abundance.

23. The method of claim 22, where said mass spectrometer utilizes atmospheric pressure ionization (API) and collision induced dissociation (CID) fragmentation.

24. The method of claim 23, where said mass spectrometer is coupled to a liquid chromatograph (LC).

25. The method of claim 23, where said multiple predefined instrument conditions are different CID voltages.

26. The method of claim 23, where the mass spectrometer is tuned with one or more tuning compounds prior to acquiring the multiple independent spectra.

27. A computer readable medium, said computer readable medium including instructions to cause a computer to perform the following functions:
  (i) receive multiple independent spectra for an unknown chemical obtained under multiple instrument conditions, each spectra having an x and y axis;
  (ii) renumber the units on the x-axis of at least one of the independent spectra so that the x-axes of the independent spectra do not perfectly overlap;
  (iii) generate a composite spectrum for the unknown chemical from said independent spectra by aligning the x-axes of the independent spectra on a composite x-axis; and
  (iv) compare the composite spectrum of the unknown chemical to the composite spectra of one or more known chemicals.

28. The computer readable medium of claim 27, which additionally includes a reference library of composite spectra for known chemicals.

29. The computer readable medium of claim 27, which additionally includes a library of individual spectra for known chemicals and instructions to cause a computer to derive a reference library of composite spectra from said library of individual spectra.

30. The computer readable medium of claim 27, which additionally includes instructions to cause a computer to generate a probability factor quantifying the probability that the unknown chemical corresponds to a known chemical.

31. The computer readable medium of claim 27, where step (iv) utilizes a pattern matching algorithm.

32. A device for identifying an unknown chemical including the following components:
  (i) a spectrometer;
  (ii) a computer;

(iii) a reference library of composite spectra generated by
   (a) acquiring multiple independent spectra for a known chemical compound under multiple predefined instrument conditions, each independent spectra including an x and y axis,
   (b) renumbering the units on the x-axis of at least one of the independent spectra so that the x-axes of the independent spectra do not perfectly overlap, and
   (c) generating a composite spectrum for the known chemical compound from said independent spectra by aligning the x-axes of the independent spectra on a composite x-axis; and
(iii) a computer readable medium including instructions to cause a computer to perform the following functions (a) receive multiple independent spectra for an unknown chemical taken under multiple conditions, each of the spectra having an x and y axis,
(b) renumber the units on the x-axis of at least one of the independent spectra so that the x-axes of the independent spectra do not perfectly overlap,
(c) generate a composite spectrum for the unknown chemical from said independent spectra by aligning the x-axes of the independent spectra on a composite x-axis, and
(d) compare the composite spectrum of the unknown chemical to the composite spectra of known chemical compounds stored in the reference library.

\* \* \* \* \*